United States Patent
Raridan et al.

(10) Patent No.: US 9,216,528 B2
(45) Date of Patent: Dec. 22, 2015

(54) BI-STABLE MEDICAL SENSOR AND TECHNIQUE FOR USING THE SAME

(71) Applicant: Covidien LP, Mansfield, MA (US)

(72) Inventors: William Raridan, Pleasanton, CA (US); George L. Matlock, Pleasanton, CA (US); Joseph Coakley, Dublin, CA (US); Darius Eghbal, Oakland, CA (US)

(73) Assignee: Covidien LP, Mansfield, MA (US)

( * ) Notice: Subject to any disclaimer, the term of this patent is extended or adjusted under 35 U.S.C. 154(b) by 44 days.

(21) Appl. No.: 13/968,196

(22) Filed: Aug. 15, 2013

(65) Prior Publication Data

US 2013/0330465 A1 Dec. 12, 2013

Related U.S. Application Data

(60) Division of application No. 12/545,691, filed on Aug. 21, 2009, now Pat. No. 8,528,185, which is a continuation of application No. 11/199,525, filed on Aug. 8, 2005, now Pat. No. 7,590,439.

(51) Int. Cl.
*B29C 45/14* (2006.01)
*A61B 5/1455* (2006.01)
(Continued)

(52) U.S. Cl.
CPC ....... *B29C 45/14819* (2013.01); *A61B 5/14552* (2013.01); *A61B 5/4869* (2013.01);
(Continued)

(58) Field of Classification Search
CPC ........... B29C 45/14819; A61B 5/4869; A61B 5/14552; A61B 5/6826; A61B 5/6838; A61B 5/6843; A61B 5/14532; A61B 2562/02; A61B 2562/187; A61B 2562/12; Y10T 29/49888; Y10T 29/4998; Y10T 29/49982; Y10T 29/53039
USPC ............. 29/460, 527.1, 527.2, 709; 427/2.12, 427/2.1, 2.11; 264/272.11, 328.1; 600/344, 600/310, 323
See application file for complete search history.

(56) References Cited

U.S. PATENT DOCUMENTS

| 6,745,061 B1 | 6/2004 | Hicks et al. |
| 7,590,439 B2 | 9/2009 | Raridan et al. |

(Continued)

FOREIGN PATENT DOCUMENTS

DE  WO01/33226  * 5/2001

OTHER PUBLICATIONS

Ostmark, Ake, et al. Mobile Medical Applications Made Feasible Through Use of EIS Platforms, IMTC-Instrumentation and Measurement Technology Conference, May 20-22, 2003, pp. 292-295, Vail, Colorado.

(Continued)

*Primary Examiner* — John C Hong
(74) *Attorney, Agent, or Firm* — Fletcher Yoder PC

(57) ABSTRACT

A bi-stable sensor is provided that includes a frame upon which electrical and optical components may be disposed and a coating, such as an overmold coating, provided about the frame. A resistance-providing component is provided integral with or external to the coated bi-stable sensor such that the bi-stable sensor has two mechanically stable configurations that may be transitioned between by overcoming the resistance provided by the resistance-providing component and/or the by the coating. In one embodiment, the resistance-providing component comprises an elastic band provided about a hinge of the frame, either within or external to the coating. In one embodiment, the sensor may be placed on a patient's finger, toe, ear, and so forth to obtain pulse oximetry or other physiological measurements.

19 Claims, 5 Drawing Sheets

(51) Int. Cl.
*A61B 5/00* (2006.01)
*A61B 5/145* (2006.01)

(52) U.S. Cl.
CPC ............. *A61B5/6826* (2013.01); *A61B 5/6838* (2013.01); *A61B 5/6843* (2013.01); *A61B 5/14532* (2013.01); *A61B 2562/02* (2013.01); *A61B 2562/12* (2013.01); *A61B 2562/187* (2013.01); *Y10T 29/49888* (2015.01)

(56) References Cited

U.S. PATENT DOCUMENTS 8,528,185 B2 * 9/2013 Raridan et al. .................. 29/460
2005/0075550 A1 4/2005 Lindekugel

OTHER PUBLICATIONS

Lebak, J.W., et al., Implementation of a Standards-Based Pulse Oximeter on a Wearable, Embedded Platform, Proceeding of the 25th Annual International Conference of the IEEE EMBS, Sep. 17-21, 2003, pp. 3196-3198, Cancun, Mexico.

Kubota, H., et al., Simultaneous Monitoring of PtcCO2 and SpO2 using a Miniature earlobe sensor, Jinko Kokyo (Artificial Respiration), pp. 24-29, 2003, vol. 20, No. 1.

Nagl, L., et al., Wearable Sensor System for Wireless State-of-Health Determination in Cattle, Proceeding of the 25th Annual International Conference of the IEEE EMBS, Sep. 17-21, 2003, pp. 3012-3015, Cancun, Mexico.

Mendelson, Y. et al., Measurement Site and Photodetector Size Considerations in Optimizing Power Consumption of a Wearable Reflectance Pulse Oximeter, Proceedings of the 25th Annual International Conference of the IEEE EMBS, Sep. 17-21, 2003, pp. 3016-3019, Cancun Mexico.

Warren, Steve, et al., A Distributed Infrastructure for Veterinary Telemedicine, Proceedings of the 25th Annual International Conference of the IEEE EMBS, Sep. 17-21, 2003, pp, 1394-1397, Cancun, Mexico.

Aoyagi, Takuo, Pulse oximetry: its invention, theory, and future. Journal of Anesthesia, 2003. pp. 259-266. vol. 17.

Avidan, A., Pulse oximeter ear probe, Anaesthesia, 2003, pp. 726, vol. 58.

Itoh, K., et al., Pulse Oximeter, Toyaku Zasshi (Toyaku Journal), 2003, pp. 50-54, vol. 25, No. 8.

Matsui, A., et al., Pulse Oxirneter, Neonatal Care, 2003, pp. 38-45, vol. 16, No. 3.

Nakagawa, M., et al., Oxygen Saturation Monitor, Neonatal Monitoring, 2003, pp. 536-539, vol. 26, No. 5.

Pujary, C., et al., Photodetector Size Considerations in the Design of a Noninvasive Reflectance Pulse Oximeter for Telemedicine Applications, IEEE, 2003, pp. 148-149.

Johanson, A., Neural network for photoplethysmographic respiratory rate monitoring, Medical & Biological Engineering & Computing, 2003, pp. 242-248, vol. 41.

Reuss, James L., Factors Influencing Fetal Pulse Oximefly Performance, Journal of clinical Monitoring and Computing, 2004, pp. 13-14, vol. 18.

Mannheimer, Paul D., et al., The influence of Larger Subcutaneous Blood Vessels on Pulse Oximetry, Journal of clinical Monitoring and Computing, 2004, pp. 179-188, vol. 18.

Johnson, P.O., Patent Cooperation Treaty PCT Written Opinion of the International Searching Authority, Apr. 20, 2007, pp. 12, European Patent Office, Berlin.

* cited by examiner

FIG. 4
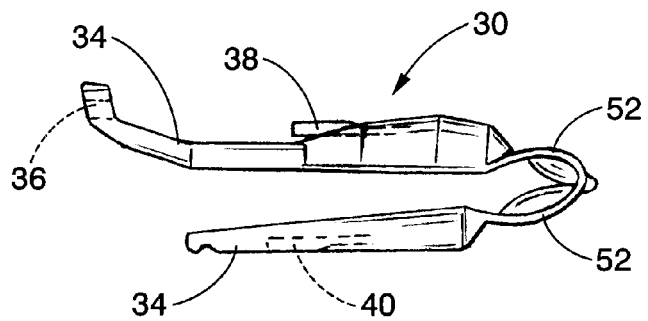
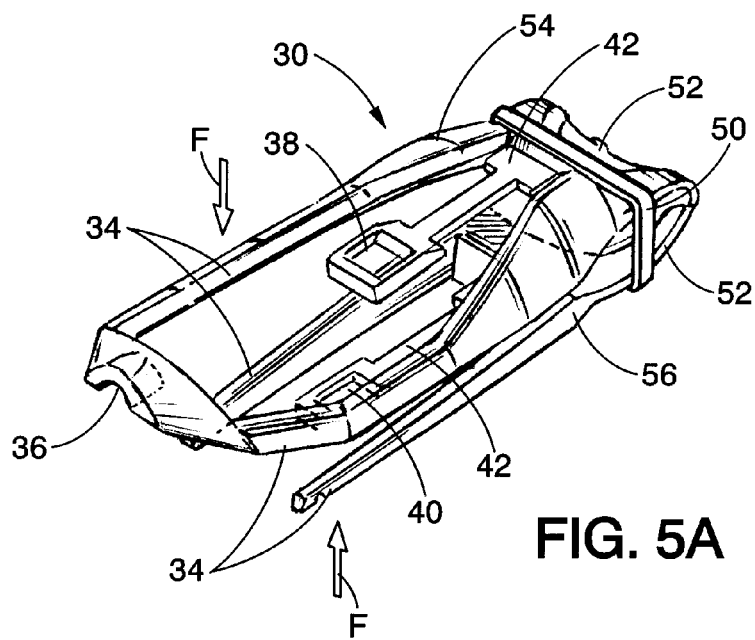
FIG. 5A
FIG. 5B
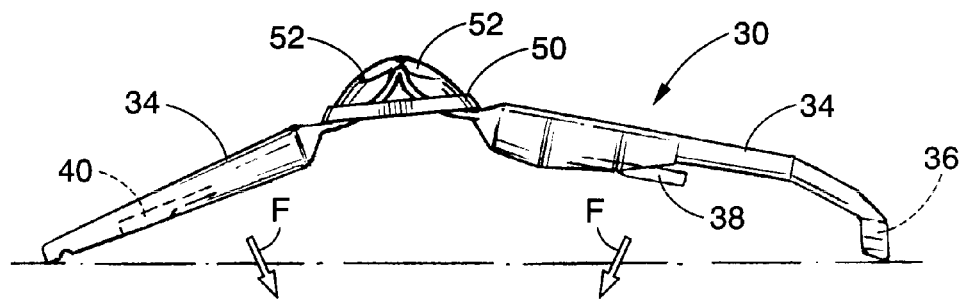

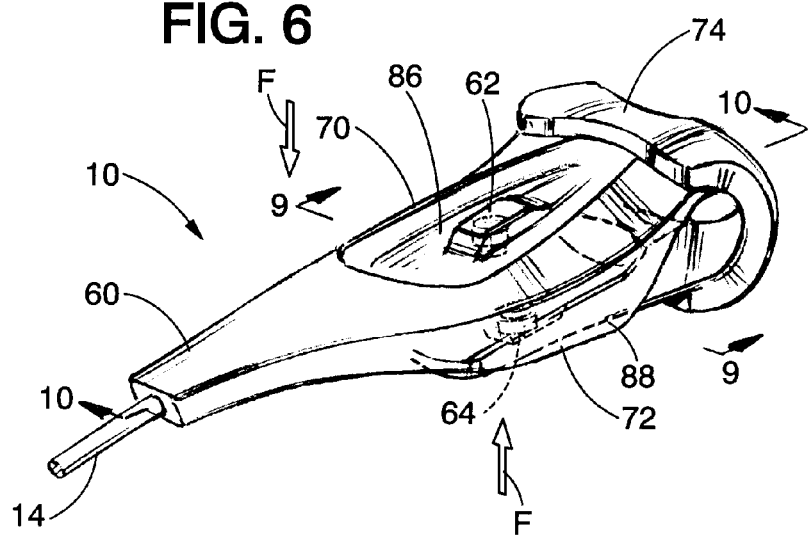
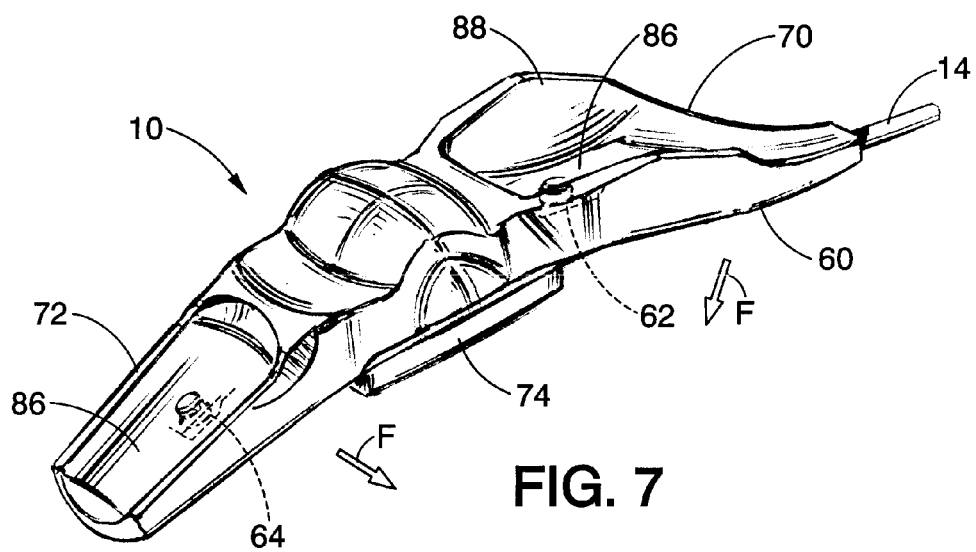

BI-STABLE MEDICAL SENSOR AND TECHNIQUE FOR USING THE SAME

This application is a divisional of U.S. patent application Ser. No. 12,545,691, entitled "Bi-Stable Medical Sensor and Technique for Using the Same", filed Aug. 21, 2009, which is a continuation of U.S. Pat. No. 7,590,439, which are herein incorporated by reference in their entirety for all purposes.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

In many instances, it may be desirable to employ, for cost and/or convenience, a pulse oximeter sensor that is reusable. Such reusable sensors, however, may be uncomfortable for the patient for various reasons. For example, the materials used in their construction may not be adequately compliant or supple or the structural features may include angles or edges.

Furthermore, the reusable sensor should fit snugly enough that incidental patient motion will not dislodge or move the sensor, yet not so tight that it may interfere with pulse oximetry measurements. Such a conforming fit may be difficult to achieve over a range of patient physiologies without adjustment or excessive attention on the part of medical personnel. In addition, lack of a tight or secure fit may allow light from the environment to reach the photodetecting elements of the sensor. Such environmental light is not related to a physiological characteristic of the patient and may, therefore, introduce error into the measurements derived using data obtained with the sensor.

Reusable pulse oximeter sensors are also used repeatedly and, typically, on more than one patient. Therefore, over the life of the sensor, detritus and other bio-debris (sloughed off skin cells, dried fluids, dirt, and so forth) may accumulate on the surface of the sensor or in crevices and cavities of the sensor, after repeated uses. As a result, it may be desirable to quickly and/or routinely clean the sensor in a thorough manner. However, in sensors having a multi-part construction, as is typical in reusable pulse oximeter sensors, it may be difficult to perform such a quick and/or routine cleaning. For example, such a thorough cleaning may require disassembly of the sensor and individual cleaning of the disassembled parts or may require careful cleaning using utensils capable of reaching into cavities or crevices of the sensor. Such cleaning is labor intensive and may be impractical in a typical hospital or clinic environment.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a sensor assembly that includes: a frame comprising two or more structural supports; a coating provided over the frame, wherein the coating comprises at least one deformable region disposed between the two or more structural supports; and at least one optical component disposed within the at least one deformable region, such that the at least one optical component can move relative to the two or more structural supports.

There is also provided a sensor assembly that includes: a frame comprising a first portion and a second portion connected by a hinge; an emitter disposed on the frame; a detector disposed on the frame; a coating provided over the frame, the emitter, and the detector to form a unitary sensor assembly; and a resistance-providing component disposed generally about the hinge.

In addition, there is also provided a sensor assembly that includes: a frame; at least one sensor component attached to the frame; and a coating provided over the frame and the at least one sensor component to form a sensor assembly having at least two mechanically stable configurations.

There is also provided a method of manufacturing a sensor that includes: situating an emitter and a detector on a skeletal frame; and coating the skeletal frame with a coating material to form a sensor assembly having at least two mechanically stable configurations.

There is also included a method for acquiring physiological data that includes: emitting two or more wavelengths of light from an emitter of a sensor assembly having at least two mechanically stable configurations; detecting transmitted or reflected light using a photodetector of the sensor assembly; and determining a physiological parameter based on the detected light.

There is also included a method of manufacturing a bi-stable sensor body that includes: coating a skeletal frame with a coating material to form a sensor body having at least two stable configurations.

There is also provided a sensor body that includes: a frame; a coating provided over the frame to form a sensor body; and a resistance-providing component configured to resist transitions between a first stable configuration and a second stable configuration of the sensor body.

There is also provided a skeletal frame of a sensor that includes: two or more structural support members having one or more spaces between the two or more structural support members, wherein the two or more structural support members are configured to provide support to an overlying coating when present; a hinge connecting some or all of the two or more structural support members; and a resistance-providing component disposed generally about the hinge such that the skeletal frame has two or more mechanically stable configurations.

BRIEF DESCRIPTION OF THE DRAWINGS

Advantages of the invention may become apparent upon reading the following detailed description and upon reference to the drawings in which:

FIG. 4 illustrates a side view of the internal frame of FIG. 2 in a closed configuration;

FIG. 5A illustrates a view of the internal frame of FIG. 2 in a closed configuration with an elastic band disposed about the hinge region;

FIG. 5B illustrates a side view of the internal frame of FIG. 2 in an open configuration with an elastic band disposed about the hinge region;

FIG. 6 illustrates an overmolded bi-stable sensor, in accordance with aspects of the present technique;

FIG. 7 illustrates the overmolded bi-stable sensor of FIG. 6 in an open configuration;

DETAILED DESCRIPTION OF SPECIFIC EMBODIMENTS

Figure 1:
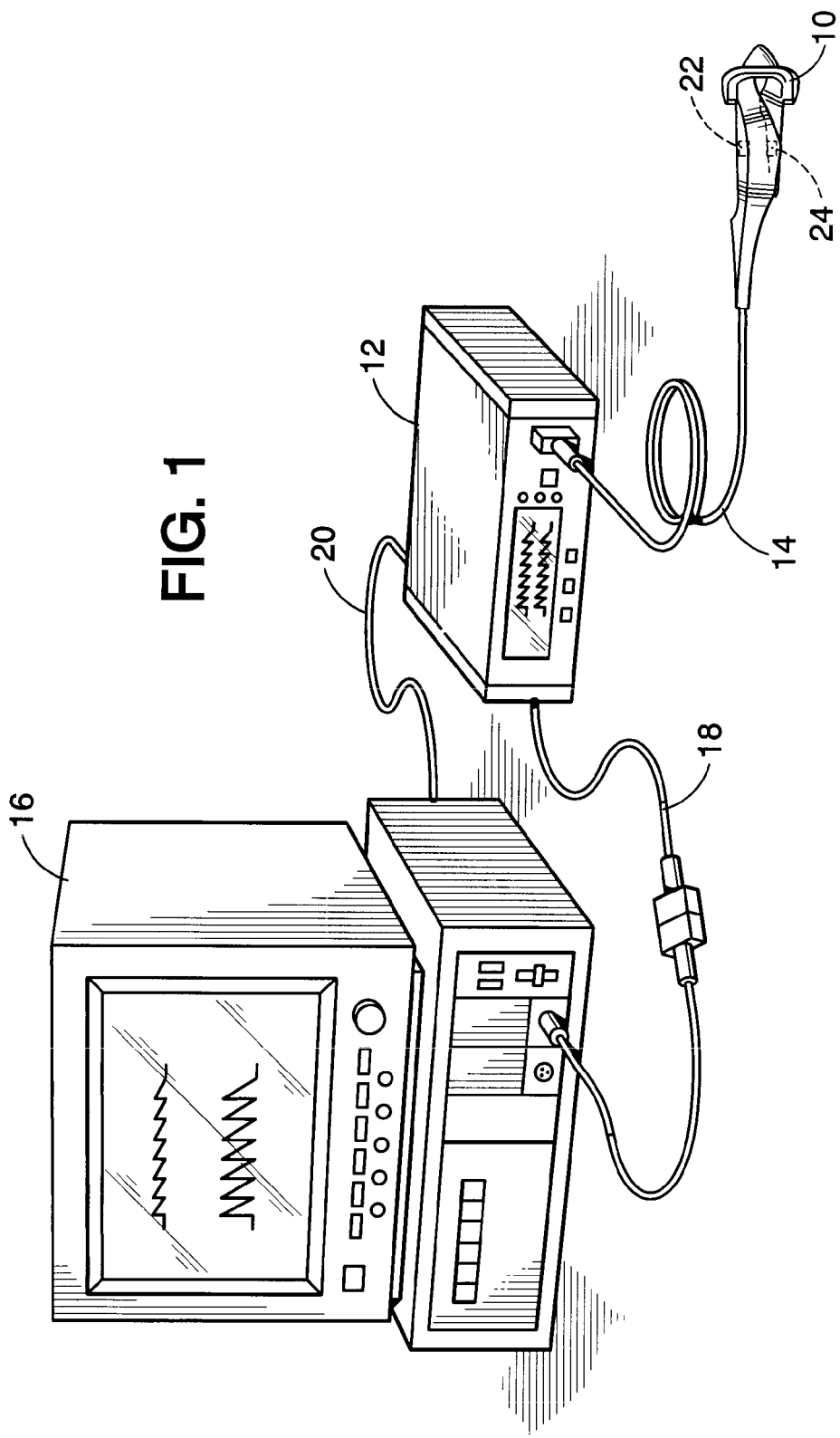
FIG. 1 illustrates a patient monitoring system coupled to a multi-parameter patient monitor and a bi-stable sensor, in accordance with aspects of the present technique.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a comfortable and conformable reusable patient sensor, such as for use in pulse oximetry or other applications utilizing spectrophotometry, that is easily cleaned and that is resistant to environmental light infiltration. In accordance with some aspects of the present technique, a reusable patient sensor is provided that is overmolded to provide patient comfort and a suitably conformable fit. The overmold material provides a seal against bodily fluids, as well as water or other cleaning fluids that allows easy cleaning without disassembly or special tools.

In accordance with some aspects of the present technique, the reusable patient sensor has more than one mechanically stable configuration, such as two-stable configurations, in a mechanically bi-stable implementation. As will be appreciated by those of ordinary skill in the art, such multi- or bi-stable configurations are resistant to transitions or movement between stable configurations, therefore each configuration is stable absent an applied force sufficient to overcome this resistance. In this way, a bi-stable device in one of its stable configurations will remain in that stable configuration until a force is applied to overcome the resistance to the transition to the second stable configuration. Once such a force is applied, however, and the bi-stable device is in the second stable configuration, the resistance now functions to resist transition back to the first stable configuration. For example, for a bi-stable sensor having open and closed configurations, the sensor will remain open until sufficient force is applied to close the sensor, however, once closed the sensor will remain closed absent a second application of force sufficient to re-open the sensor.

Prior to discussing such exemplary multi- or bi-stable sensors in detail, it should be appreciated that such sensors may be designed for use with a typical patient monitoring system. For example, referring now to FIG. 1, a bi-stable sensor 10 according to the present invention may be used in conjunction with a patient monitor 12. In the depicted embodiment, a cable 14 connects the bi-stable sensor 10 to the patient monitor 12. As will be appreciated by those of ordinary skill in the art, the sensor 10 and/or the cable 14 may include or incorporate one or more integrated circuit devices or electrical devices, such as a memory, processor chip, or resistor, that may facilitate or enhance communication between the bi-stable sensor 10 and the patient monitor 12. Likewise the cable 14 may be an adaptor cable, with or without an integrated circuit or electrical device, for facilitating communication between the bi-stable sensor 10 and various types of monitors, including older or newer versions of the patient monitor 12 or other physiological monitors. In other embodiments, the bi-stable sensor 10 and the patient monitor 12 may communicate via wireless means, such as using radio, infrared, or optical signals. In such embodiments, a transmission device (not shown) may be connected to the bi-stable sensor 10 to facilitate wireless transmission between the bi-stable sensor 10 and the patient monitor 12. As will be appreciated by those of ordinary skill in the art, the cable 14 (or corresponding wireless transmissions) are typically used to transmit control or timing signals from the monitor 12 to the bi-stable sensor 10 and/or to transmit acquired data from the bi-stable sensor 10 to the monitor 12. In some embodiments, however, the cable 14 may be an optical fiber that allows optical signals to be conducted between the monitor 12 and the bi-stable sensor 10.

In one embodiment, the patient monitor 12 may be a suitable pulse oximeter, such as those available from Nellcor Puritan Bennett Inc. In other embodiments, the patient monitor 12 may be a monitor suitable for measuring tissue water fractions, or other body fluid related metrics, using spectrophotometric or other techniques. Furthermore, the monitor 12 may be a multi-purpose monitor suitable for performing pulse oximetry and measurement of tissue water fraction, or other combinations of physiological and/or biochemical monitoring processes, using data acquired via the sensor 10. Furthermore, to upgrade conventional monitoring functions provided by the monitor 12 to provide additional functions, the patient monitor 12 may be coupled to a multi-parameter patient monitor 16 via a cable 18 connected to a sensor input port and/or via a cable 20 connected to a digital communication port.

The sensor 10, in the example depicted in FIG. 1, is a bi-stable sensor that is overmolded to provide a unitary or enclosed assembly. The bi-stable sensor 10 includes an emitter 22 and a detector 24 which may be of any suitable type. For example, the emitter 22 may be one or more light emitting diodes adapted to transmit one or more wavelengths of light, such as in the red to infrared range, and the detector 24 may be a photodetector, such as a silicon photodiode package, selected to receive light in the range emitted from the emitter 22. In the depicted embodiment, the bi-stable sensor 10 is coupled to a cable 14 that is responsible for transmitting electrical and/or optical signals to and from the emitter 22 and detector 24 of the bi-stable sensor 10. The cable 14 may be permanently coupled to the bi-stable sensor 10, or it may be removably coupled to the bi-stable sensor 10—the latter alternative being more useful and cost efficient in situations where the bi-stable sensor 10 is disposable.

The bi-stable sensor 10 described above is generally configured for use as a "transmission type" sensor for use in spectrophotometric applications, though in some embodiments it may instead be configured for use as a "reflectance type sensor." Transmission type sensors include an emitter and detector that are typically placed on opposing sides of the sensor site. If the sensor site is a fingertip, for example, the bi-stable sensor 10 is positioned over the patient's fingertip such that the emitter and detector lie on either side of the patient's nail bed. For example, the bi-stable sensor 10 is positioned so that the emitter is located on the patient's fingernail and the detector is located opposite the emitter on the patient's finger pad. During operation, the emitter shines one or more wavelengths of light through the patient's fingertip, or other tissue, and the light received by the detector is processed to determine various physiological characteristics of the patient.

Reflectance type sensors generally operate under the same general principles as transmittance type sensors. However, reflectance type sensors include an emitter and detector that are typically placed on the same side of the sensor site. For example, a reflectance type sensor may be placed on a patient's fingertip such that the emitter and detector are positioned side-by-side. Reflectance type sensors detect light photons that are scattered back to the detector.

For pulse oximetry applications using either transmission or reflectance type sensors the oxygen saturation of the patient's arterial blood may be determined using two or more wavelengths of light, most commonly red and near infrared wavelengths. Similarly, in other applications a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

Pulse oximetry and other spectrophotometric sensors, whether transmission-type or reflectance-type, are typically placed on a patient in a location conducive to measurement of the desired physiological parameters. For example, pulse oximetry sensors are typically placed on a patient in a location that is normally perfused with arterial blood to facilitate measurement of the desired blood characteristics, such as arterial oxygen saturation measurement ($SaO_2$). Common pulse oximetry sensor sites include a patient's fingertips, toes, forehead, or earlobes. Regardless of the placement of the bi-stable sensor 10, the reliability of the pulse oximetry measurement is related to the accurate detection of transmitted light that has passed through the perfused tissue and has not been inappropriately supplemented by outside light sources or modulated by subdermal anatomic structures. Such inappropriate supplementation and/or modulation of the light transmitted by the sensor can cause variability in the resulting pulse oximetry measurements.

As noted above, the bi-stable sensor 10 discussed herein may be configured for either transmission or reflectance type sensing. For simplicity, the exemplary embodiment of the bi-stable sensor 10 described herein is adapted for use as a transmission-type sensor. As will be appreciated by those of ordinary skill in the art, however, such discussion is merely exemplary and is not intended to limit the scope of the present technique.

Referring now to FIGS. 2-5, an internal frame 30 for a bi-stable sensor 10 is depicted. In the depicted example, the internal frame 30 is a skeletal frame for a bi-stable sensor 10. Such a skeletal frame may include different structures or regions that may or may not have similar rigidities. For example, the depicted skeletal frame includes structural supports 34 that define the general shape of the sensor 10 when coated, as discussed below with regard to FIGS. 6-10. In view of their structure providing function, the structural supports 34 may be constructed to be substantially rigid or semi-rigid. In addition, the skeletal frame may include a cable guide 36 through which a cable, such as an electrical or optical cable, may pass to connect to the electrical or optical conductors attached to the emitter 22 and/or detector 24 upon assembly. Likewise, a skeletal frame, such as the depicted internal frame 30, may include component housings, such as the emitter housing 38 and detector housing 40 and struts 42 attaching such housings to the remainder of the skeletal frame. The struts 42 may be relatively flexible, allowing the emitter housing 38 and/or the detector housing 40 to move vertically (such as along an optical axis between the respective housings) relative to the structural supports 34 of the skeletal frame. Alternatively, in embodiments where the struts 42 are relatively rigid, where multiple struts 42 are employed to attach the housings 38 and 40 to the structural supports 34, or where the internal frame is substantially solid instead of skeletal, the housings 38 and/or 40 may be fixed relative to the respective structural supports 34 and, therefore, move with the structural supports 34.

Figure 2:
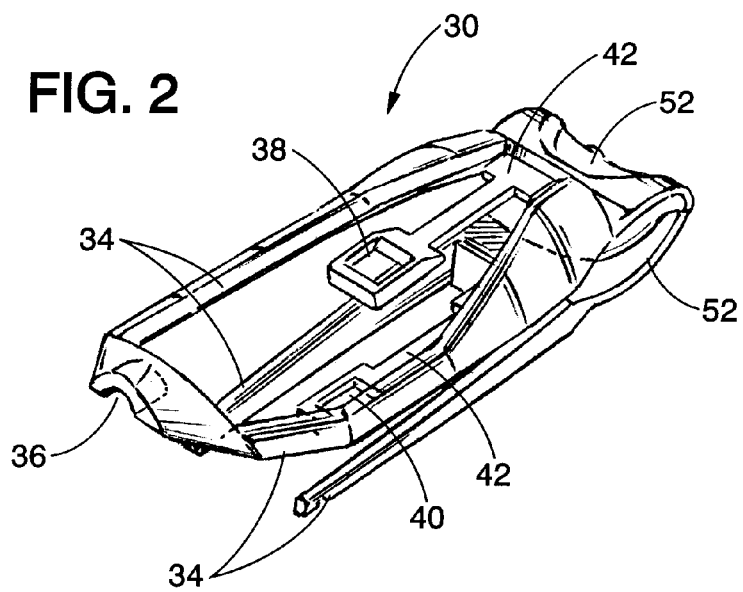
FIG. 2 illustrates a closed internal frame for use in a bi-stable sensor, in accordance with aspects of the present technique.

In embodiments where the internal frame 30 is skeletal, the various structural supports 34, housings 38 and 40, struts 42, and other structures may define various openings and spaces between and/or around the structures of the skeletal frame. In this manner, the skeletal frame provides structural support at specific locations for a coating or overmolding. However, in regions where structural support is not provided, flexibility and freedom of motion in an overlying coating or overmolding may be possible. For example, in one implementation, the emitter housing 38 and/or the detector housing 40 may be attached to the remainder of the skeletal frame by flexible struts 42, as depicted in FIG. 2. In such implementations, a coating provided proximate to the emitter housing 38 and/or detector housing 40 may be sufficiently flexible (such as due to the elasticity and/or the thinness of the coating material in the open areas of the skeletal frame) such that the housings 38 and 40 may move independent of the structural supports 34 of the frame 30 along an optical axis between the housings 38 and 40.

In certain embodiments, the internal frame 30 is constructed, in whole or in part, from polymeric materials, such as thermoplastics, capable of providing a suitable rigidity or semi-rigidity for the different portions of the internal frame 30. Examples of such suitable materials include polyurethane, polypropylene and nylon, though other polymeric materials may also be suitable. In other embodiments, the internal frame 30 is constructed, in whole or in part, from other suitably rigid or semi-rigid materials, such as stainless steel, aluminum, magnesium, graphite, fiberglass, or other metals, alloys, or compositions that are sufficiently ductile and/or strong. For example, metals, alloys, or compositions that are suitable for diecasting, sintering, lost wax casting, stamping and forming, and other metal or composition fabrication processes may be used to construct the internal frame 30.

In addition, the internal frame 30 may be constructed as an integral structure or as a composite structure. For example, in one embodiment, the internal frame 30 may be constructed as a single piece from a single material or from different materials. Alternatively, the internal frame 30 may be constructed or assembled from two or more parts that are separately formed. In such embodiments, the different parts may be formed from the same or different materials. For example, in implementations where different parts are formed from different materials, each part may be constructed from a material having suitable mechanical and/or chemical properties for that part. The different parts may then be joined or fitted together to form the internal frame 30.

Figure 3:
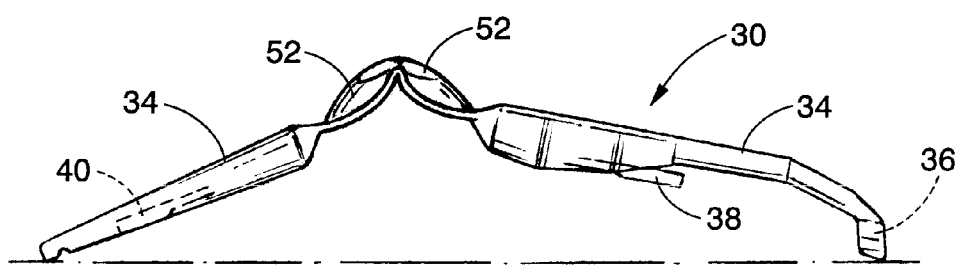
FIG. 3 illustrates a side view of the internal frame of FIG. 2 in an open configuration.

In addition, the internal frame 30 may be molded, formed, or constructed in a different configuration than the final sensor configuration. For example, the internal frame 30 for use in the bi-stable sensor 10 may be initially formed in a generally open, or flat, configuration, as depicted in FIG. 3. The internal frame 30 may then be bent from the open configuration into a relatively closed configuration, as depicted in FIG. 4.

In certain embodiments, the internal frame 30 is fitted with a resistance component, such as an elastic band 50 fitted about a hinge region 52, as depicted in FIGS. 5A and 5B. The resistance component provides or augments a resistance to transitions between configurations of the bi-stable sensor 10, as depicted generally by arrows generally indicative of the direction force (F) is applied by the resistance component. That is, the resistance provided or augmented by the resistance component is overcome to transition between two mechanically stable sensor configurations. For example, in FIG. 5A, the resistance component provides force, F, that biases a first portion 54 and a second portion 56 of the internal frame 30 closed absent a greater opposing force, i.e., an opening force. Likewise, in FIG. 5B, the resistance component provides force, F, that biases the first portion 54 and second portion 56 of the internal frame 30 apart absent a greater opposing force, i.e., a closing force.

As will be appreciated by those of ordinary skill in the art, a resistance component, such as elastic band 50, may be composed of a material or a combination of materials that provide the desired elasticity and resistance, such as polymeric materials (rubber, plastic, and so forth) or metals. Likewise, the resistance component may take other forms than a continuous loop, such as the exemplary elastic band 50. For example, an elastic band or strap may be configured with dove-tailed ends or with a dog-bone shape to facilitate connection to the frame 30, such as to conform to complementary attachment regions integral to the frame 30.

Though the present example depicts the resistance component, in the form of elastic band 50, as being disposed directly on the frame 30, one of ordinary skill in the art will appreciate that other configurations are also possible. For example, the resistance component, such as elastic band 50, may be disposed within a coating material overlying the frame 30 or external to such a coating material. Similarly, in other embodiments, the resistance component may be provided as part of the frame 30, such as a hinge portion 52 configured to resist transitions between stable configurations (without augmentation by an added resistance component). Likewise, the resistance component may be or may include an elastomeric coating material, as discussed below, disposed over the frame 30. In such embodiments, the coating material may provide the resistance based on the elasticity or other physical properties of the coating material itself. Alternatively, the resistance provided by the coating may be based on regions of the coating that differ in elasticity and/or hardness, thereby forming resistive structures or regions within the coating.

As noted above, in certain embodiments of the present technique, the frame 30 (such as a skeletal, internal frame) is coated to form a unitary or integral sensor assembly, as depicted in FIGS. 6-10. Such overmolded embodiments may result in a sensor assembly in which the internal frame 30 is completely or substantially coated. In embodiments in which the internal frame 30 is formed or molded as a relatively open or flat structure, the overmolding or coating process may be performed prior to or subsequent to bending the internal frame 30 into the closed configuration.

For example, the bi-stable sensor 10 may be formed by an injection molding process. In one example of such a process the internal frame 30, with or without an attached elastic band 50, may be positioned within a die or mold of the desired shape for the bi-stable sensor 10. A molten or otherwise unset overmold material may then be injected into the die or mold. For example, in one implementation, a molten thermoplastic elastomer at between about 400° F. to about 450° F. is injected into the mold. The overmold material may then be set, such as by cooling for one or more minutes or by chemical treatment, to form the sensor body about the internal frame 30 and the elastic band 50, if present. In certain embodiments, other sensor components, such as the emitter 22 and/or detector 24, may be attached or inserted into their respective housings or positions on the overmolded sensor body.

Alternatively, the optical components (such as emitter 22 and detector 24) and/or conductive structures (such as wires or flex circuits) may be placed on the internal frame 30 prior to overmolding. The internal frame 30 and associated components may then be positioned within a die or mold and overmolded, as previously described. To protect the emitter 22, detector 24, and or other electrical components, conventional techniques for protecting such components from excessive temperatures may be employed. For example, the emitter 22 and/or the detector 24 may include an associated clear window, such as a plastic or crystal window, in contact with the mold to prevent coating from being applied over the window. In one embodiment, the material in contact with such windows may be composed of a material, such as beryllium copper, which prevents the heat of the injection molding process from being conveyed through the window to the optical components. For example, in one embodiment, a beryllium copper material initially at about 40° F. is contacted with the windows associated with the emitter 22 and/or detector 24 to prevent coating of the windows and heat transfer to the respective optical components. As will be appreciated by those of ordinary skill in the art, the injection molding process described herein is merely one technique by which the frame 30 may be coated to form a sensor body, with or without associated sensing components. Other techniques which may be employed include, but are not limited to, dipping the frame 30 into a molten or otherwise unset coating material to coat the frame 30 or spraying the frame 30 with a molten or otherwise unset coating material to coat the frame 30. In such implementations, the coating material may be subsequently set, such as by cooling or chemical means, to form the coating. Such alternative techniques, to the extent that they may involve high temperatures, may include thermally protecting whatever optical components are present, such as by using beryllium copper or other suitable materials to prevent heat transfer through the windows associated with the optical components, as discussed above.

By such techniques, the frame 30, as well as the optical components and associated circuitry where desired, may be encased in a coating material 60 to form an integral or unitary assembly with no exposed or external moving parts of the frame 30. For example, as depicted in FIGS. 6 and 7, the bi-stable sensor 10 includes features of the underlying internal frame 30 that are now completely or partially overmolded, such as the overmolded emitter housing 62 and detector housing 64. In addition, the overmolded bi-stable sensor 10 includes an overmolded upper portion 70 and lower portion 72 that may be fitted to the finger, toe, ear, or other appendage of a patient when the bi-stable sensor 10 is in a closed configuration.

In one implementation, the overmolding or coating 60 is a thermoplastic elastomer or other conformable coating or material. In such embodiments, the thermoplastic elastomer may include compositions such as thermoplastic polyolefins, thermoplastic vulcanizate alloys, silicone, thermoplastic polyurethane, and so forth. As will be appreciated by those of ordinary skill in the art, the overmolding composition may vary, depending on the varying degrees of conformability, durability, wettability, elasticity, or other physical and/or chemical traits that are desired.

Figure 8:
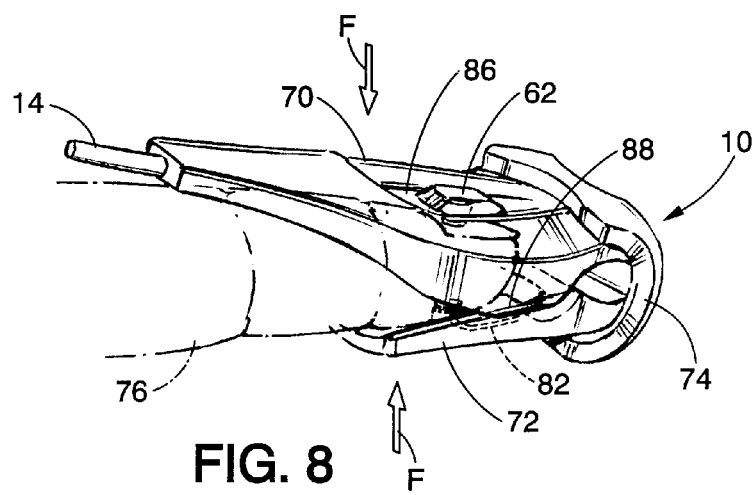
FIG. 8 illustrates the bi-stable sensor of FIG. 6 in use on a patient's finger, in accordance with aspects of the present technique.

Furthermore, the coating material 60 may be selected or configured to provide some or all of the resistance to transitions of the bi-stable sensor 10 between open and closed configurations, as depicted in FIGS. 6 and 7. For example, referring now to FIGS. 6 and 7, the coating material 60 may be disposed as a thick region 74 or layer about the hinge region of the bi-stable sensor (generally corresponding to the overmolded hinge region 52 of the frame 30). In this manner, the thickness of the thick region 74 and the elasticity of the coating material 60 may provide resistance, indicated by force arrows, F, which opposes transitions between different configurations of the bi-stable sensor 10. For example, as depicted in FIG. 7, in an open configuration, the resistance provided by the thick region 74 of coating material acts to bias the upper portion 70 and lower portion 72 of the sensor body 10 apart. A sufficient opposing or closing force, however, may overcome the resistance provided by the thick region 74 of coating material, to transition the sensor body 10 a closed configuration, as depicted in FIG. 6. Once in the closed configuration, the thick region 74 of coating material then resists transition to the open configuration, as indicated by force arrows, F, in FIG. 6. As will be appreciated by those of ordinary skill in the art, in the closed configuration, the upper portion 70 and lower portion 72 may be partially separated without fully overcoming the resistance to transition, i.e., without "opening" the sensor 10, allowing the sensor 10 to be comfortably and conformably fitted to a patient's finger 76, as depicted in FIG. 8, or to a patient's toe, ear, and so forth, in other embodiments.

The depicted sensor 10, therefore, has two mechanically stable configurations, i.e., it is bi-stable, with each stable configuration resisting change absent a force sufficient to overcome the resistance provided by the sensor itself. As will be appreciated by those of ordinary skill in the art, the resistance to transitioning between stable configurations may depend on various factors, such as those described by example herein. For example, to the extent that the resistance is provided at least partly by a thick region 74 of coating material, as depicted in FIGS. 6 and 7, the resistance may be a function of the thickness of the thick region 74, the elasticity and/or hardness of the coating material 60, and the presence of additional resistive structure within or about the thick region 74. For instance, the thick region 74 may be composed of coating material 60 having uniform composition, elasticity, hardness, and so forth. Alternatively, the thick region 74 may be composed of more than one type of coating material 60, with the different coating materials having different elasticities, hardnesses, or other mechanical properties that affect the resistance to transition between stable configurations of the sensor 10. Furthermore, the thick region 74 of coating material may overlie, incorporate, or support an additional resistive structure, such as an elastic band 50 disposed about the hinge region 52 of the frame. Therefore, as will be appreciated by those of ordinary skill in the art, the resistance opposing transitions between stable configurations of the sensor 10 may be determined by a variety of factors, such as the thickness of the coating material 60 about a hinge of the sensor 10, the composition, configuration, and/or uniformity of the coating material 60 about the hinge of the sensor 10, the construction or inclusion of additional resistive structures about the hinge of the sensor 10, as well as other possible factors.

While selection of the coating material 60 may be based upon the resistance considerations noted above, the coating material 60 may also be selected based upon the desirability of a chemical bond between the internal frame 30 and the coating material 60. Such a chemical bond may be desirable for durability of the resulting overmolded bi-stable sensor 10. For example, to prevent separation of the coating 60 from the internal frame 30, the material used to form the coating 60 may be selected such that the coating 60 bonds with some or all of the internal frame 30 during the overmolding process. In such embodiments, the coating 60 and the portions of the internal frame 30 to which the coating 60 is bonded are not separable, i.e., they form one continuous and generally inseparable structure.

Furthermore, in embodiments in which the coating 60 employed is liquid or fluid tight, such a bi-stable sensor 10 may be easily maintained, cleaned, and/or disinfected by immersing the sensor into a disinfectant or cleaning solution or by rinsing the sensor 10 off, such as under running water. For example, in an open configuration of the sensor 10, as depicted in FIG. 7, and the sensor 10 may be immersed or rinsed with water or a disinfectant solution for easy cleaning. Of course, the bi-stable sensor 10 may be cleaned in either the closed or open configuration. In particular, the overmolded bi-stable sensor 10 may be generally or substantially free of crevices, gaps, junctions or other surface irregularities typically associated with a multi-part construction which may normally allow the accumulation of biological detritus or residue. Such an absence of crevices and other irregularities may further facilitate the cleaning and care of the sensor 10.

Figure 9:
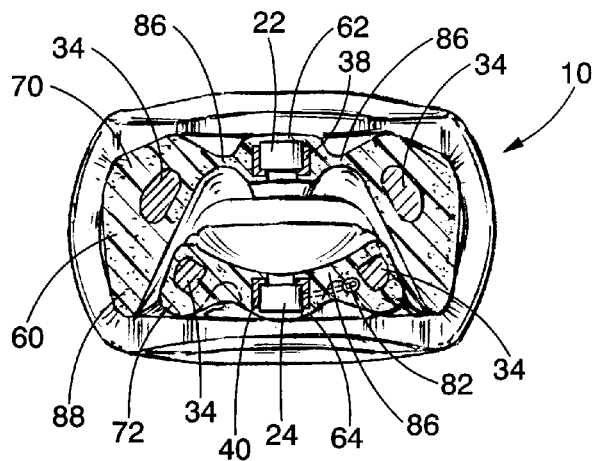
FIG. 9 illustrates a cross-section taken along section line 9 of FIG. 6.
Figure 10:
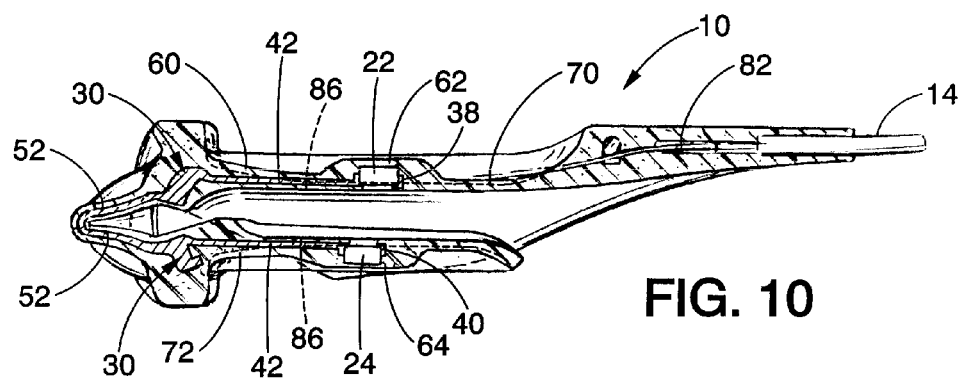
FIG. 10 illustrates a cross-section taken along section line 10 of FIG. 6.

Turning now to FIGS. 9 and 10, cross-sections of the coated bi-stable sensor 10 in a closed configuration are depicted taken through transverse optical planes, represented by section line 8 and 9 of FIG. 6 respectively. FIGS. 8 and 9 depict, among other aspects of the bi-stable sensor 10, the overmolding material 60 as well as underlying portions of the internal frame 30, such as the emitter housing 38 and detector housing 40, along with the respective emitter 22, detector 24, and signal transmission structures (such as wiring 82 or other structures for conducting electrical or optical signals). In the depicted embodiment, the emitter 22 and detector 24 are provided substantially flush with the patient facing surfaces of the bi-stable sensor 10, as may be suitable for pulse oximetry applications. For other physiological monitoring applications, such as applications measuring tissue water fraction or other body fluid related metrics, other configurations may be desirable. For example, in such fluid measurement applications it may be desirable to provide one or both of the emitter 22 and detector 24 recessed relative to the patient facing surfaces of the bi-stable sensor 10. Such modifications may be accomplished by proper configuration or design of a mold or die used in overmolding the internal frame 30 and/or by proper design of the emitter housing 38 or detector housing 40 of the internal frame 30.

In addition, as depicted in FIGS. 9 and 10, in certain embodiments portions 86 of the coating material 60 may be flexible, such as thin or membranous regions of coating material 60 disposed between structural supports 34 of a skeletal frame. Such flexible regions 86 allow a greater range of digit sizes to be accommodated for a given retention or clamping force of the sensor 10. For example, the flexible regions 86 may allow the emitter 22 and/or detector 24, to flex or expand apart from one another along the optical axis in embodiments in which the respective housings 38 and 40 are flexibly attached to the remainder of the frame 30. In this manner, the sensor 10 may accommodate differently sized digits. For instance, for a relatively small digit, the flexible regions 86 may not be substantially deformed or vertically displaced, and therefore the emitter 22 and/or detector 24 are not substantially displaced either. For larger digits, however, the flexible regions 86 may be deformed or displaced to a greater extent to accommodate the digit, thereby displacing the emitter 22 and/or detector 24 as well. In addition, for medium to large digits, the flexible regions 86 may also increase retention of the sensor 10 on the digit by increasing the surface area to which the retaining force is applied.

Furthermore, as the flexible regions 86 deform, the force applied to the digit is spread out over a large area on the digit due to the deformation of the flexible region 86. In this way, a lower pressure on digits of all sizes may be provided for a given vertical force. Therefore, a suitable conforming fit may be obtained in which the emitter 22 and detector 24 are maintained in contact with the digit without the application of concentrated and/or undesirable amounts of force, thereby improving blood flow through the digit.

In the example depicted in FIGS. 6-10, flaps or side extensions 88 of the coating material 60 on the sides of the bi-stable sensor 10 are depicted which facilitate the exclusion of environmental or ambient light from the interior of the bi-stable sensor 10. Such extensions help prevent or reduce the detection of light from the outside environment, which may be inappropriately detected by the sensor 10 as correlating to the $SaO_2$. Thus, the pulse oximetry sensor may detect differences in signal modulations unrelated to the underlying $SaO_2$ level. In turn, this may impact the detected red-to-infrared modulation ratio and, consequently, the measured blood oxygen saturation ($SpO_2$) value. The conformability of the fit of sensor 10 and the use of side extensions 88, therefore, may help prevent or reduce such errors.

While the exemplary bi-stable sensors 10 discussed herein are some examples of overmolded or coated medical devices, other such devices are also contemplated and fall within the scope of the present disclosure. For example, other medical sensors and/or contacts applied externally to a patient may be advantageously applied using a bi-stable sensor body as discussed herein. Examples of such sensors or contacts may include glucose monitors or other sensors or contacts that are generally held adjacent to the skin of a patient such that a conformable and comfortable fit is desired. Similarly, and as noted above, devices for measuring tissue water fraction or other body fluid related metrics may utilize a sensor as described herein. Likewise, other spectrophotometric applications where a probe is attached to a patient may utilize a sensor as described herein.

In addition, overmolded bi-stable medical devices for use invasively, i.e., within the patient, are also presently contemplated. For example, clamps or other medical devices used invasively may be designed as bi-stable devices, i.e., having an open and a closed position, in which the transition between configurations is accomplished using a substantial force, thereby preventing incidental or accidental transitions between open and closed configurations. Furthermore, an overmolding or other coating may be provided on such devices, such as where non-reactivity with bodily fluids or tissues is desired, or where it is generally desired to provide an invasive device having few or no exposed niches or crevices or where it is generally desired to coat the internal framework or skeleton of a device.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to transmission type sensors for use in pulse oximetry, but also to retroflective and other sensor designs as well. Likewise, the present techniques are not limited to use on fingers and toes but may also be applied to placement on other body parts such as in embodiments configured for use on the ears or nose.

What is claimed is:

1. A method of manufacturing a bi-stable sensor body, comprising:
   positioning a skeletal frame within a mold; and
   coating the skeletal frame with a coating material to form a sensor body having at least two stable configurations.

2. The method of claim 1, wherein the skeletal frame is substantially open when coated.

3. The method of claim 1, wherein the skeletal frame is substantially closed when coated.

4. The method of claim 1, comprising attaching a resistance-providing component about a hinge on the skeletal frame prior to coating the skeletal frame.

5. The method of claim 1, comprising attaching a resistance-providing component about a coated hinge of the sensor body.

6. The method of claim 1, comprising bending the skeletal frame from a relatively open configuration to a relatively closed configuration prior to coating.

7. The method of claim 1, comprising bending the skeletal frame from a relatively open configuration to a relatively closed configuration subsequent to coating.

8. The method of claim 1, wherein coating the skeletal frame comprises injecting an unset coating material into the mold.

9. A method of manufacturing a sensor body, comprising: disposing a frame within a mold, wherein the frame has at least two mechanically stable configurations such that a resistance must be overcome to transition between the mechanically stable configurations; and injecting or blowing a molding material into the mold such that the molding material coats the frame to form an overmolded sensor body.

10. The method of claim 9, comprising attaching a resistance component to the frame prior to coating.

11. The method of claim 10, wherein the resistance component comprises a hinge.

12. The method of claim 10, wherein the resistance component has a thicker coating than a coating on the frame.

13. The method of claim 9, wherein the molding material provides additional resistance after being applied to the frame.

14. The method of claim 9, comprising chemically bonding the molding material to the frame.

15. The method of claim 9, comprising positioning an emitter and a detector on the frame prior to coating.

16. The method of claim 9, comprising molding the frame in an substantially open configuration.

17. The method of claim 9, comprising bending the frame to form a substantially closed configuration after molding.

18. The method of claim 9, wherein the frame is constructed of a single piece.

19. The method of claim 9, wherein the frame is assembled from two or more separable pieces.

* * * * *